United States Patent [19]

Lundy

[11] Patent Number: 5,636,387
[45] Date of Patent: Jun. 10, 1997

[54] PROTECTIVE UNDERGARMENT

[76] Inventor: Al T. Lundy, P.O. Box 2714, Big Spring, Tex. 79721

[21] Appl. No.: 437,238

[22] Filed: May 8, 1995

[51] Int. Cl.$^6$ ................................................ A41B 9/04
[52] U.S. Cl. ................... 2/408; 2/406; 2/400; 450/102; 604/385.1; 604/395
[58] Field of Search ............................. 2/400, 401, 402, 2/403, 406, 407, 408, 78.1, 78.2, 78.3, 78.4, 79; 450/102, 103, 104; 128/883; 604/385.1, 395, 396

[56] References Cited

U.S. PATENT DOCUMENTS

| | | | |
|---|---|---|---|
| 875,845 | 1/1908 | Perkins | 128/883 |
| 1,179,159 | 4/1916 | Buley . | |
| 1,830,528 | 11/1931 | Cohon | 450/103 |
| 1,967,233 | 7/1934 | Fellroth . | |
| 2,396,599 | 3/1946 | O'Brien | 2/408 |
| 2,443,474 | 6/1948 | Morgan . | |
| 2,896,633 | 7/1959 | McKee | 450/104 X |
| 2,998,011 | 8/1961 | Rubin | 450/104 |
| 3,208,454 | 9/1965 | Farkas | 2/408 X |
| 3,279,469 | 10/1966 | Schustack | 2/408 X |
| 3,974,836 | 8/1976 | Carlson | 2/408 |
| 4,164,217 | 8/1979 | Schrock . | |
| 4,599,751 | 7/1986 | Bouwhuis . | |
| 4,835,795 | 6/1989 | Lonon . | |
| 4,951,321 | 8/1990 | Mortensen et al. | 2/408 |
| 5,157,790 | 10/1992 | Aldridge . | |
| 5,341,515 | 8/1994 | Cohen | 2/400 |

*Primary Examiner*—Jeanette E. Chapman
*Attorney, Agent, or Firm*—Stephen R. Greiner

[57] ABSTRACT

A penetration resistant undergarment in the form of pants for preventing sexual assault upon a wearer. The pants have a front portion and a back portion secured together so as to define a narrowed waist and a pair of laterally-spaced legs remote therefrom. An elongated opening extending between the laterally-spaced legs to a point in the front portion proximate the narrowed waist is selectively closed by a protective flap secured to the back portion of the pants. The protective flap has a tubular sleeve at is free end through which a waist belt may be drawn. A locking mechanism secured to the pants locks the waist belt snugly against the narrowed waist.

10 Claims, 1 Drawing Sheet

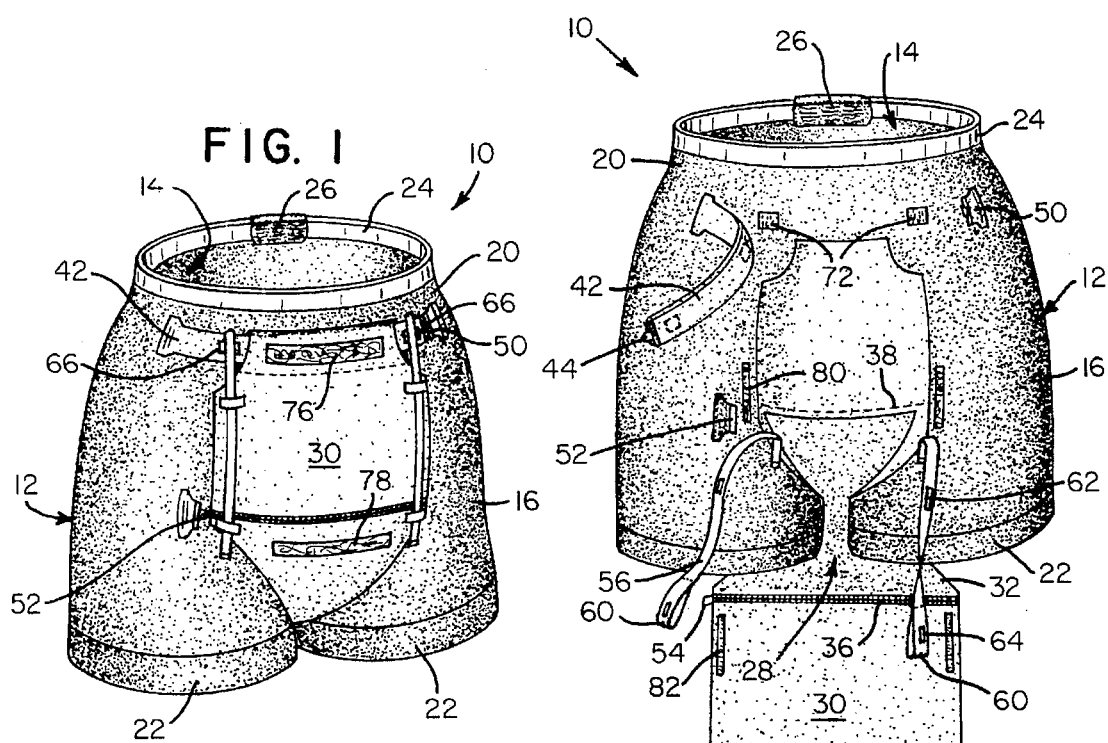
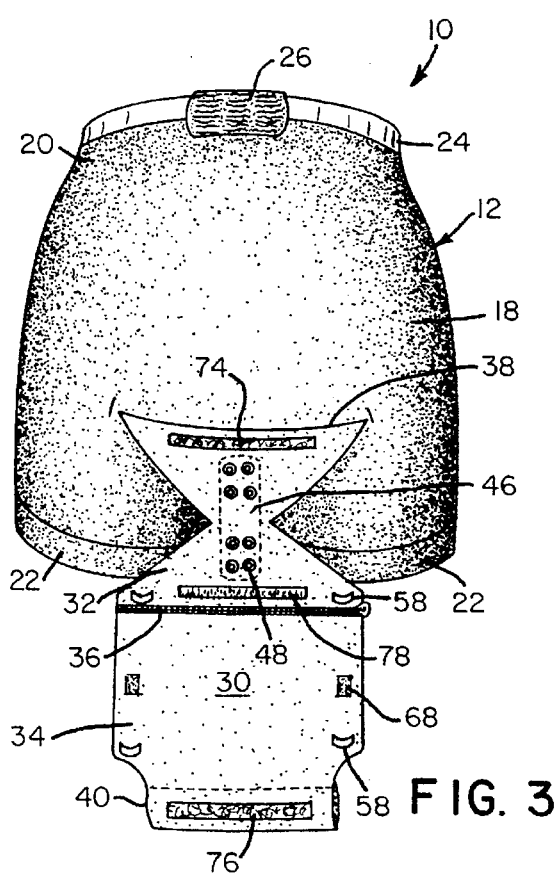
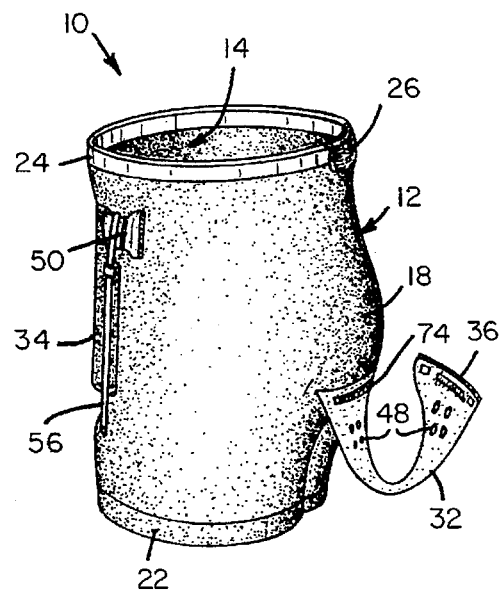

5,636,387

PROTECTIVE UNDERGARMENT

FIELD OF THE INVENTION

The present invention relates generally to a penetration resistant undergarment for preventing sexual assault upon a wearer.

BACKGROUND OF THE INVENTION

The numbers of sexual assaults upon males and females have been increasing for years. Thus, many individuals have resorted to carrying concealed weapons such as firearms, knives and small tear gas canisters for personal protection. Unfortunately, the generally low level of skill in using such weapons presented by most law-abiding citizens makes it likely that an attacker will gain possession of the weapon during an assault and utilize it to incapacitate the original user.

In an effort to reduce the need for law-abiding citizens to each carry a relatively dangerous weapon on a continuous basis, various articles of clothing have been heretofore proposed as sexual assault deterrents of a passive type. In the main, these clothing articles have been bulky, heavy in weight and, as such, uncomfortable to wear even for limited periods of time. A need, therefore, exists for a lightweight and comfortable, protective undergarment which may be discretely worn for as long as may be desired by a wearer.

SUMMARY OF THE INVENTION

In light of the foregoing need, it is a principal object of the present invention to provide a lightweight and comfortable undergarment in the form of pants for personal protection against sexual assault. When worn under an article or clothing such as trousers or a skirt, the protective undergarment is a hidden deterrent capable of significantly decreasing the likelihood of a successful sexual assault upon a wearer.

It is another object of the invention to provide a protective undergarment of the type described that permits a wearer to urinate or defecate without the garment being fully removed or soiled. To this end, a protective flap for selectively closing an elongated opening in the pants is a feature of the invention. The protective flap has a tubular sleeve at its free end through which a waist belt may be selectively drawn and locked. To attend to bodily functions, the belt need merely be unlocked and withdrawn from the tubular sleeve for the protective flap to be removed from the elongated opening.

Still another object of the invention is to provide improved elements and arrangements thereof in a protective undergarment for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

The present invention may be more readily described with reference to the accompanying drawings, in which:

FIG. 1 is a perspective view of a protective undergarment in accordance with the present invention.

FIG. 2 is a front elevational view of the protective undergarment of FIG. 1 shown with its protective flap in an opened position.

FIG. 3 is a rear elevational view of the protective undergarment shown with its protective flap in an opened position.

FIG. 4 is a side elevational view of the protective undergarment shown with its protective flap bifurcated by its associated zipper.

Similar reference characters denote corresponding features consistently throughout the accompanying drawings.

DETAILED DESCRIPTION OF THE PREFERRED EMBODIMENT

Referring now to the figures, a protective undergarment 10 in accordance with the present invention is shown. The preferred undergarment 10 comprises a pair of pants for covering the body of a wearer from the waist to the upper thighs having a protective shell 12 and a close-fitting inner liner 14 sewn, or otherwise secured, thereto. Preferably, the protective shell 12 is made from a woven aramid fiber such as KEVLAR which is resistant to cutting or tearing so that the undergarment cannot be removed by such a method. For comfort, the inner liner 14, dimensioned to cover substantially the entire inner surface of the protective shell 12, is preferably made from a hydrophobic fabric such as COOLMAX. Any suitable fabric that promotes moisture evaporation and body cooling, however, may be used to form the inner liner 14.

The protective shell 12 is preferably constructed in accordance with conventional fabric weaving and sewing techniques such that it includes a front portion 16 and a back portion 18 integrally formed from a single piece of fabric. Alternatively, the protective shell may be formed from separate front and back portions sewn together in well-known fashion. Regardless of the method used to construct the protective shell 12, the conjoined front portion 16 and back portion 18 define a relatively narrow waist 20 in the protective shell 12 and a pair of laterally-spaced legs 22 remote therefrom.

A waist band 24 is preferably sewn about the waist 20 of the protective shell 12 for reinforcement purposes. The waist band 24 is preferably made from an elongated strip of KEVLAR material which has been folded upon itself to at least double its thickness for added strength. As shown, the free ends of the KEVLAR strip are preferably centrally disposed in opposing fashion adjacent the back portion 18 a short distance from one another. To the opposing free ends of the KEVLAR strip as well as the back portion 18 is secured a relatively short elastomeric patch 26 thus permitting the protective undergarment 10 to be readily donned by allowing the waist band 24 to yield somewhat when pulled upon. The elastomeric patch 26 also retains the waist band 24 snugly against the body of a wearer during use.

The protective shell 12 is provided with an elongated opening 28 extending from the crotch region between the legs 22 to a point proximate the waist band 24 where secured to the front portion 16. This opening 28 may be selectively opened by a wearer by means of a protective flap 30 preferably formed of KEVLAR and lined as desired. By preferably providing the flap 30 with a size somewhat larger than that of the opening 28, so that the flap overlaps the front and back portions 16 and 18 when in a closed position as shown in FIG. 1, direct access to the sex organs of a wearer is effectively prevented.

With particular reference now to FIG. 3, the flap 30 may best be seen to include an hourglass-shaped crotch panel 32 adapted to fit without binding between the thighs of a wearer and a generally rectangular front panel 34 secured thereto by means of a zipper 36. As shown, one end of the crotch panel 32 is attached to the center of the back portion 18 by means of a sewn seam 38. At the opposing end of the flap 30, in the front panel 34, is provided a tubular sleeve 40 for the transverse passage of a waist belt 42 and its associated catch 44. For added comfort, a moisture absorbent pad 46 is secured to the crotch panel 32 and adapted for positioning against the body of the wearer. The absorbent pad 46 may, of course, be disposed beneath a suitable liner if desired. A plurality of grommets 48 line holes through the crotch panel 32 and moisture absorbent pad 46 to conduct air into the protective undergarment 10 for ventilation purposes.

Like the protective shell 12, the preferred waist belt 42 is formed from a flexible material that is both cut and tear resistant such as KEVLAR. Optionally, the waist belt 42 may be lined, or otherwise reinforced, with a strip of metal foil (not shown) such as one comprising, for instance, titanium of suitable thickness to further increase its overall strength and durability. In the preferred embodiment, the waist belt 42 is provided with a sufficient length to snugly engage the outer surface of the front portion 16 and flap 30 when locked in place.

A locking mechanism for securing the belt 42 across the abdomen of the wearer while it is extended through the tubular sleeve 40 is illustrated generally at 50. The locking mechanism 50 may be of any suitable construction and may utilize a key or combination-type mechanism. One key-type lock for belts believed to be suitable for use in the locking mechanism 50 of instant invention is illustrated in U.S. Pat. No. 4,599,751, issued Jul. 15, 1986, to Harry E. Bouwhuis which is hereby incorporated by reference for all purposes.

The zipper 36 connecting the panels 32 and 34 of the flap 30 together may also be provided with a locking mechanism 52 to secure the sliding zipper tab 54 thereof to the front panel 16 of the protective shell 12 so that it may not be unintentionally moved to disengage the previously interlocked rows of zipper teeth. The locking mechanism 52 may be of any suitable construction known in the art or may be an appropriately modified form of the Bouwhuis apparatus referred to hereinabove.

The protective undergarment 10 preferably has a pair of tie straps 56 which can be of KEVLAR construction for retaining the lateral edges of the front panel 34 snugly against the front portion 16 of the protective shell 12. As shown, the bottom of each tie strap 56 is sewn securely to a leg 22 so that such may be extended upwardly in overlapping fashion upon the front panel 34. Fabric loops 58 secured to the panels 32 and 34 of the flap 30 assist in retaining the tie straps 56 in an upright orientation. The top of each tie strap 56, extending above the loops 58, is provided with a tubular sleeve 60 for receiving the waist belt 42. Preferably, each of the tie straps 56 is of sufficient length to receive the waist belt 42 when horizontally positioned for locking with a minimum of slack.

On the inner surface of each tie strap 56 is provided a pair of loop-type fastening strips 62 and 64. As shown in FIG. 2, the fastening strips 64 are disposed adjacent the tubular sleeve 60 whereas the fastening strips 62 are disposed proximate the tie strap midpoint. When it is desired that the tie straps 56 be carried in an upright orientation without engagement of the tubular sleeves 60 with the waist belt 42, the fastening strips 62 and 64 may be engaged with counterpart, hook-type fastening strips 66 and 68 provided, respectively, to the outer surface of waist belt 42 and the front panel 34 of the flap 30.

The protective undergarment 10 is provided with strips of hook-and-loop fastening material for "quick release" of the protective flap 30 when the locking mechanisms 50 and 52 are disengaged. In this regard, the inner surface of the tubular sleeve 40 is provided with a pair of loop-type fastening strips 70 which cooperate with hook-type fastening strips 72 adjacent the waist band 24 on the front portion 16 of the protective shell 12 to retain the flap 30 in a closed position when the strips 70 and 72 are mated together. In the usual fashion, the flap 30 may be opened when the strips 70 and 72 are pulled apart by a wearer.

To permit the wearer of the protective undergarment 10 to urinate or defecate without impedance by the flap 30, additional hook-and-loop fastening strips are provided thereto. To the crotch panel 32 near the attachment seam 38, then, is secured a strip 74 comprising loop-type fastening material. A cooperating strip 76 of hook-type material is secured to the outer surface of the front panel 43 adjacent the tubular sleeve 40. Thus, the flap 30 may be folded back upon itself and the cooperating fastening strips 74 and 76 secured together so that the flap is out of the way and is not in a position to be soiled.

A similar hook-type fastening strip 78 is secured to the crotch panel 32 of the flap 30 adjacent the zipper 36. When the crotch panel 32 is unfastened from the front panel 34 by means of the zipper 36, its free end may also be folded back and secured to the fastening strip 74 so that such is out of the way and is not in a position to be soiled.

Cooperating strips of hook-and-loop fastening material 80 and 82 are also preferably provided to the protective undergarment 10 to secure the front panel 34 against the body of the wearer should the crotch panel 32 be disengaged therefrom by opening the zipper 36. As shown, the front portion 16 of the protective shell 12 is suitably provided with hook-type strips 80 on opposite sides of the opening 28 while the lower corners of the front panel 34 are provided with loop-type strips 82. As the lower corners of the front panel 34 overlap the front portion 16 of the protective shell 12, the fastening strips 80 and 82 may be readily positioned for mated engagement.

For use, the protective undergarment 10 of the invention is donned by an individual in the usual manner directly in contact with the skin or, alternatively, outside a conventional undergarment. Preferably, the protective undergarment 10 should fit snugly about the hips, thighs and buttocks of a wearer. Of course, to accomplish a snug fit, the protective undergarment 10 can be sized differently to fit men, women and children.

After placing the protective undergarment 10 upon the body of a wearer, the waist belt 42 is drawn through the tubular sleeves 60 and 40 of the tie straps 56 and flap 30, respectively. The selected locking mechanism 50 is then utilized to secure the catch 44 of the belt 42 to the outer surface of the front portion 16. Upon locking, the protective undergarment 10 cannot be removed in the absence of a key or special tools not normally carried by persons intent upon perpetrating a sexual attack. A wearer, of course, will ensure that the zipper locking mechanism 52 is also secured when full protection of the protective undergarment is desired.

Bodily functions may be readily attended to by opening the protective flap 30. As should now be apparent, the flap 30 may be opened simply by disengaging both of the locking mechanisms 50 and 52 and moving the flap 30 away from the opening 28 as desired. In the alternative, the crotch panel 32 of the flap 30 may be more rapidly opened as shown in FIG. 4 by releasing the singular locking mechanism mechanism 52 and opening the zipper 36.

When the threat of sexual assault is minimal, the protective flap 30 and tie straps 56 may be retained in a generally closed position by means of the various hook-and-loop fastening strips described hereinabove. These hook-and-loop fastening strips may be disengaged from one another by pulling so as to open the flap 30 in seconds. As explained, additional hook-and-loop strips may then be used to retain the flap 30 in a convenient location. Thus, it is believed that the protective undergarment 10 can be worn at all times with a minimum of inconvenience.

While the invention has been described with a high degree of particularity, it will be appreciated by those skilled in the art that numerous modifications and substitutions may be made thereto. Of course, the protective undergarment would be fully effective in accomplishing its intended purposes in the absence any cooperating hook-and-loop fastening strips or the tie straps 56. Nevertheless, such features are believed to significantly enhance the utility of the undergarment. Therefore, it is to be understood that the present invention is not limited to the sole embodiment described above, but encompasses any and all embodiments within the scope of the following claims.

I claim:

1. A protective undergarment, comprising:

pants having a front portion and a back portion secured together so as to define a narrowed waist and a pair of laterally-spaced legs remote therefrom, said pants having an opening extending between said laterally-spaced legs to a point in said front portion proximate said narrowed waist;

a protective flap secured to said back portion of said pants and adapted to close said opening, said protective flap having a first tubular sleeve at its free end, said protective flap further including:

a crotch panel positioned between said laterally spaced legs;

a front panel having said first tubular sleeve; and, a zipper for selectively securing said crotch panel to said front panel;

a waist belt having one end secured to said pants adjacent said narrowed waist and a free end adapted to be drawn through said tubular sleeve when said protective flap is in a closed position;

a first locking mechanism secured to said pants for locking said waist belt snugly against said narrowed waist; and, a second locking mechanism secured to said pants for maintaining said zipper in a closed orientation.

2. The protective undergarment according to claim 1 further comprising a pair of cooperating hook-and-loop fastening strips including:

a first strip of hook-type fastening material secured to said front panel on said first tubular sleeve; and, a first strip of loop-type fastening material secured to said crotch panel.

3. A protective undergarment, comprising:

pants having a front portion and a back portion secured together so as to define a narrowed waist and a pair of laterally-spaced legs remote therefrom, said pants having an opening extending between said laterally-spaced legs to a point in said front portion proximate said narrowed waist;

a protective flap secured to said back portion of said pants and adapted to close said opening, said protective flap having a first tubular sleeve at is free end, said protective flap further including:

a crotch panel positioned between said laterally spaced legs;

a front panel having said first tubular sleeve; and, a zipper for selectively securing said crotch panel to said front panel;

a waist belt having one end secured to said pants adjacent said narrowed waist and a free end adapted to be drawn through said tubular sleeve when said protective flap is in a closed position;

a first locking mechanism secured to said pants for locking said waist belt snugly against said narrowed waist;

a pair of cooperating hook-and-loop fastening strips including a first strip of hook-type fastening material secured to said front panel on said first tubular sleeve and a first strip of loop-type fastening material secured to said crotch panel; and, a second strip of hook-type fastening material secured to said crotch panel remote from said first strip of loop-type fastening material and adapted for selective mated engagement with said first strip of loop-type fastening material.

4. The protective undergarment according to claim 1 further comprising a pair of tie straps each having one end secured to one of said laterally-spaced legs, each of said tie straps having a second tubular sleeve at its free end for receiving said waist belt.

5. The protective undergarment according to claim 1 wherein said pants are formed from a flexible material resistant to tearing and cutting.

6. The protective undergarment according to claim 5 wherein said flexible material comprises a woven aramid fiber.

7. A protective undergarment, comprising:

pants having a front portion and a back portion secured together so as to define a narrowed waist and a pair of laterally-spaced legs remote therefrom;

said pants having an opening extending between said laterally-spaced legs to a point in said front portion proximate said narrowed waist;

a protective flap secured to said back portion of said pants and adapted to close said opening, said protective flap having a crotch panel positioned between said laterally-spaced legs and a front panel releasably secured to said crotch panel, said front panel having a first tubular sleeve at its free end;

a waist belt secured to said pants adjacent said narrowed waist and adapted to be drawn through said first tubular sleeve when said protective flap is in a closed position;

a first locking mechanism secured to said pants for locking said waist belt snugly against said narrowed waist;

a pair of cooperating hook-and-loop fastening strips including a first strip of hook-type fastening material secured to said front panel on said first tubular sleeve and a first strip of loop-type fastening material secured to said crotch panel; and, a second strip of hook-type fastening material secured to said crotch panel remote from said first strip of loop-type fastening material and adapted for selective mated engagement with said first strip of loop-type fastening material.

8. The protective undergarment according to claim 7 further comprising a pair of tie straps each having one end secured to one of said laterally-spaced legs, each of said tie straps having a second tubular sleeve at its free end for receiving said waist belt.

9. The protective undergarment according to claim 7 wherein said pants are formed from a flexible material resistant to tearing and cutting.

10. The protective undergarment according to claim 9 wherein said flexible material comprises a woven aramid fiber.

* * * * *